United States Patent [19]

Coulter et al.

[11] Patent Number: 4,791,355

[45] Date of Patent: Dec. 13, 1988

[54] PARTICLE ANALYZER FOR MEASURING THE RESISTANCE AND REACTANCE OF A PARTICLE

[75] Inventors: Wallace H. Coulter, Miami Springs; Carlos M. Rodriguez, Miami, both of Fla.

[73] Assignee: Coulter Electronics Inc., Hialeah, Fla.

[21] Appl. No.: 921,654

[22] Filed: Oct. 21, 1986

[51] Int. Cl.$^4$ ............................................. G01N 27/00
[52] U.S. Cl. ............................... 324/71.1; 324/61 QS; 324/61 R
[58] Field of Search .................. 324/71.1, 71.4, 61 R, 324/61 QS, 61 QL, 985; 340/562, 609

[56] References Cited

U.S. PATENT DOCUMENTS

| 2,230,297 | 2/1941 | Inoui | 324/71.1 |
| 2,411,247 | 11/1946 | Cohen | 324/61 QS |
| 3,502,974 | 3/1970 | Coulter et al. | 324/71.1 |
| 4,298,836 | 11/1981 | Groves et al. | 324/71.1 |
| 4,525,666 | 6/1985 | Groves | 324/71.1 |
| 4,535,284 | 8/1985 | Groves et al. | 324/71.1 |
| 4,710,757 | 12/1987 | Haase | 324/61 R |

FOREIGN PATENT DOCUMENTS

WO85/05684 12/1985 PCT Int'l Appl. .

OTHER PUBLICATIONS

Hoffman and Britt, "Flow System Measurement of Cell Impedance Properties", *Journal of Histrochemistry and Cytochemistry*, vol. 27, No. 1, pp. 234–240, (1979).
Lief et al., "Two Dimensional Impedence Studies of BSA Buoyant Density Separated Human Erythrocytes", *Cytometry*, vol. 6, pp. 13–21. (1983).
Hellman and Benjamin, "The Toa Micro Cell Counter", Scand. J. Haemat., pp. 67–76, (1969) 6.
Code, "NMR Q-Meter Detectors", *Rev. Sci. Instrum.*, vol. 46, No. 6, pp. 661–665, (1975).
Robinson & Phil, "Nuclear Resonance Absorption Circuit", *Journal of Scientific Instruments*, vol. 39, pp. 481–487, (1959).
Hughes & Smith, "On the Nuclear Magnetic Resonance Detection Characteristics of Marginal and Robinson Oscillators", Journal of Physics E: Scientific Instruments, pp. 13–20, (1971).
Weber and Town, "Single Tube Nuclear Quadrupole Spectrometer for Chlorine and Nitrogen".

O'Tonski & Schaffer, "A Wide Range Superregenative Nuclear Quadrupole Resonance Spectrometer", The Review of Scientific Instruments, vol. 42, No. 12, pp. 1891–1892, (1971).
Yogi et al., "NMR Marginal Oscillator with MOS-FET Operating at Low Temperature", Japanese Journal of Applied Physics, vol. 12, No. 11, pp. 1794–1798, (1978).
Lee and Choh, "Robinson-Type Nuclear Quadrupole Resonance Spectrometer Adapted to Field-Effect Transistors", Rev. Sci. Instrument, vol. 53, No. 2, pp. 232–235, (1982).
"Oscillators", McGraw Hill Encyclopedia of Scientific Technology, pp. 419–425.

*Primary Examiner*—M. H. Paschall
*Assistant Examiner*—A. Jonathan Wysocki
*Attorney, Agent, or Firm*—Harry W. Barron; Gerald R. Hibnick

[57] ABSTRACT

A circuit, which is useful to provide data needed to measure the electrical opacity of a particle, for instance a blood cell, passing through a Coulter type transducer, includes a current source for providing a conventional d.c. current through the sensing aperture of the transducer, as well as an oscillator for providing a high frequency current through the aperture. The oscillator includes an active device and a resonant circuit, and the aperture is coupled in parallel with the resonant circuit of the oscillator. The oscillator can be any type of oscillator, such as a Hartley oscillator. As a particle passes through the aperture, the resistance of the aperture increases, which in turn, increases the Q of the oscillator circuit, whereby the oscillator output signal is amplitude modulated in accordance with the increased Q. This amplitude modulated signal can be detected to provide a value based on the high frequency reactance of the particle being detected. The change in d.c. resistance due to a particle passing through the aperture is detected in a conventional manner. The detected amplitudes of the a.c. and d.c. signals then can be compared to determine the opacity of each particle. Multiple oscillators of different frequencies can be coupled in parallel with the transducer through a coupling circuit, which connects each oscillator to the transducer through a low impedance path and isolates each oscillator from signals having frequencies of the other oscillators.

33 Claims, 2 Drawing Sheets

PARTICLE ANALYZER FOR MEASURING THE RESISTANCE AND REACTANCE OF A PARTICLE

BACKGROUND OF THE INVENTION

This invention relates to an improved particle analyzer and more particular to such a particle analyzer adapted for measuring the resistance and reactance of a particle, such as a blood cell, in order to determine the electrical opacity of the particle.

As is well known in the art, the electrical opacity of a blood cell has been defined as the ratio of the a.c. impedance to the d.c. resistance of the cell. Apparatus to provide data which enables the electrical opacity of the cell to be measured was first proposed in U.S. Pat. No. 3,502,974 in the name of Wallace H. Coulter and Walter R. Hogg and entitled "Signal Modulated Apparatus For Generating And Detecting Resistive And Reactive Changes In A Modulated Current Path For Particle Classification And Analysis". Such opacity parameter can be used in a number of different fashions to obtain certain results when analyzing blood cells. Examples of use of opacity are described in U.S. Pat. No. 4,298,836 in the name of Michael R. Groves et al and entitled "Particle Shape Determination", U.S. Pat. No. 4,525,666 in the name of Michael R. Groves and entitled "Cell Breakdown" and U.S. Pat. No. 4,535,284 in the name of Michael R. Groves et al entitled "High And Low Frequency Analysis Of Osmotic Stress Of Cells". Each of the above noted U.S. patents have been assigned to the assignee of the present invention. In addition, uses for opacity have been described PCT Published Application WO85/05684, also assigned to the assignee hereof, and in the articles entitled "Flow System Measurement Of Cell Impedance Properties", R. A. Hoffman and W. B. Britt, *The Journal of Histrochemistry and Cytochemistry*, Volume 27, Number 1, pages 234–240 (1979) and "Two Dimensional Impedance Studies of BSA Buoyant Density Separated Human Erythrocytes", R.C. Leif, et al. *Cytometry*, Volume 6, Pages 13–21 (1985).

A unique apparatus and principle of blood cell counting and sizing was invented by Wallace H. Coulter and is described in U.S. Pat. No. 2,656,508. According to the Coulter principle, a fluid electrolyte containing particles, such as blood cells, passes from one chamber to another chamber through a small orifice or aperture. An electrode is placed in each of the chambers and a direct current, or low frequency current is applied to the electrodes and through the orifice, thereby creating an electric field in the orifice. As a particle, or blood cell, traverses the orifice, the resistance within the orifice is changed. This resistance can be sensed by sensing the voltage across the electrodes, whereby the presence of a particle in the orifice causes a pulse in the voltage being sensed by the electrodes.

The Coulter principle, first described in the aforementioned U.S. Pat. No. 2,656,508, has been expanded by additionally providing a high frequency current through the orifice at the same time that the low frequency, or direct current, signal is passed through the orifice. By appropriate filtering techniques, both the low frequency resistance and high frequency reactances of the cell traversing the orifice can be detected. Such detection has been described in more detail in the aforementioned articles and the United States Patents as the structure used to obtain the data for determining the opacity. In addition, cells can be detected using the high frequency current alone and in so doing, additional information can be obtained based on the fact that the amplitude of the pulse varies in response to the frequency of the current through the orifice.

One of the problems with the prior art structure has been interference created between the two separate current sources used to create the a.c. and d.c. fields within the orifice. One way the prior art teaches coupling the low frequency, or d.c. current source, and the high frequency current source is in parallel to one another and in parallel with the electrodes sensing the particle in the orifice. However, this type of coupling can lead to interference between the two sources. This is particularly true where multiple high frequency oscillators are utilized, such as described in U.S. Pat. No. 3,502,974. Where two high frequency tuned circuits are coupled across the orifice, any slight change in conditions can cause either, or both, of the two frequencies to become detuned. For example, a drift in the temperature or pressure of the fluid, or a bubble within the orifice, can result in problems with the above circuitry. This problem is illustrated in the type of machine described in the article entitled "The Toa Micro Cell Counter" by P. W. Helleman and C. J. Benjamin, *Scand. J. Haemat.* (1969) 6, pages 69–76, where the oscillator tuned circuit and the detector tuned circuit are separately coupled in parallel in the circuit. Because of this instability, the devices of the prior art have not been able to achieve commercial success, despite having been known for at least fifteen years. In order to render the principle of detecting data sufficient to provide the opacity or high frequency response of a blood cell particle practical, improvements are required in both the oscillator circuitry and means for connecting the oscillator circuitry in circuit with the remainder of the traditional Coulter type transducer.

SUMMARY OF THE INVENTION

In accordance with one aspect of this invention, there is provided a particle analyzer comprising detector means through which a series of particles pass. The detector means has a certain resistance and reactance, at least one of which changes as a particle passes therethrough. In addition, the analyzer includes high frequency oscillator means, including an active device and a resonant circuit. The resonant circuit is coupled to the detector means so that the detector means resistance and reactance are included as a part of the resonant circuit. Lastly, the particle analyzer includes means for sensing any change in the output signal of the oscillator as a result of a particle passing through the detector means.

In accordance with a second aspect of this invention, there is provided a particle analyzer for determining the presence and certain parameters of particles in solution comprising detector means through which the solution passes, the detector means having a certain resistance and reactance at least one of which changes as the particle passes therethrough. Further, the invention includes a plurality of oscillator means, each providing a different frequency signal, and coupling means for coupling each of the oscillator means in parallel with the detector means. The coupling means includes reactance means associated with each oscillator means and arranged and valued so that the signal provided by each oscillator means is coupled through a low impedance path to the detector means and through a high impedance path to the other plurality of oscillator means. Finally, the invention includes means for manifesting the presence of and the certain parameters for each of the frequencies whenever a particle passes through the detector.

BRIEF DESCRIPTION OF THE DRAWINGS

One preferred embodiment of the subject invention is hereafter described with specific reference being made to the following Figures, in which.

DETAILED DESCRIPTION

Figure 1:
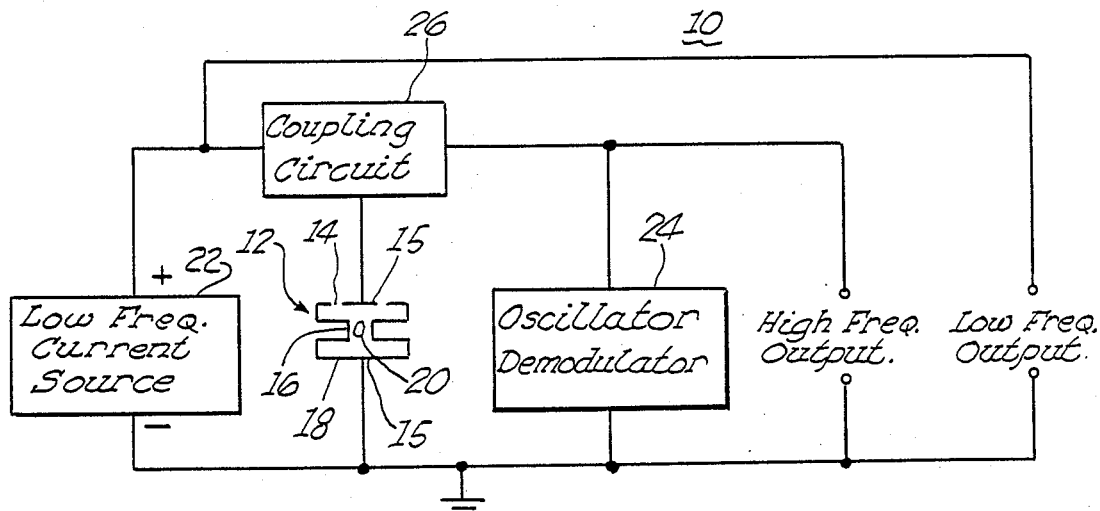
FIG. 1 is a block diagram of the improved particle analyzer.

Referring now to FIG. 1, a block diagram of the improved particle analyzer 10 is shown. The heart of analyzer 10 includes a Coulter transducer 12 well known in the art. Briefly, transducer 12 includes a holding chamber 14, an orifice 16, a receiving chamber 18, and an electrode 15 in each chamber. A fluid, containing particles to be tested, is placed in holding chamber 14. The fluid passes through orifice 16 so that the particles, such as blood cells 20, pass through orifice 16 one at a time. The fluid, including the particles, then is held in receiving chamber 18.

In order to detect blood cell 20 passing through orifice 16, a low frequency current source 22 is coupled to provide current through orifice 16. This can be accomplished by coupling a battery in series with a resistor, thereby providing the d.c. current source between the electrodes 15 in holding chamber 14 and receiving chamber 18 of Coulter transducer 12. At the same time, the voltage across orifice 16 is monitored by sensing the voltage across electrodes 15. Each time a blood cell 20 passes through orifice 16, the increased resistance due to the cell causes the voltage between electrodes 15 to increase, thereby creating a pulse in the voltage signal sensed.

In order to obtain the electrical opacity of blood cell 20, it is necessary to couple a high frequency oscillator/demodulator 24 across orifice 16. High frequency oscillator/demodulator 24 can be a conventional high Q oscillator, which includes both an active device and a resonant circuit. Oscillator/demodulator 24 is coupled to electrodes 15 so that orifice 16 is coupled in parallel with the resonant circuit portion of the oscillator portion of circuit 24. This will be described in more detail hereafter in FIG. 2.

In order to prevent the high frequency signal from oscillator/demodulator 24 and the low frequency signal from current source 22 from interfering with one another, it is essential to apply both signals through a coupling circuit 26 prior to coupling them to electrodes 15. Coupling circuit 26 also isolates the two outputs from one another. The details of coupling circuit 26 will be described hereafter with respect to FIG. 2.

Figure 2:
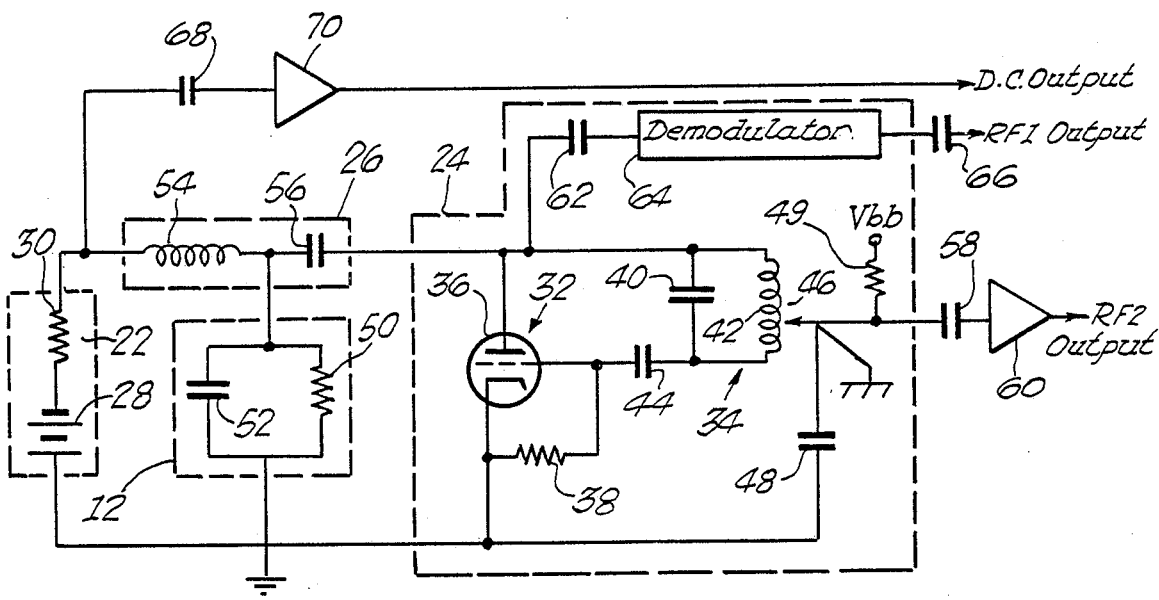
FIG. 2 is a circuit diagram, partially in block form, of the particle analyzer shown in FIG. 1.

Referring now to FIG. 2, the detailed circuit arrangement of the particle analyzer, shown in block form in FIG. 1, will now be described. In FIG. 2, the four principal component parts of the FIG. 1 block diagram are shown in dashed lines and labeled with like numerical designations. Low frequency current source 22 simply can consist of a source of d.c. voltage 28 coupled serially with a resistor 30. Thus, a constant d.c. current is provided from low frequency current source 22.

Oscillator/demodulator 24 includes both an active device portion 32 and a resonant circuit portion 34. These two portions constitute a conventional oscillator circuit, such as a Hartley oscillator, well known in the art. The circuit components of oscillator/demodulatro 24 are selected so that the oscillator portion has a relatively high Q. The active device shown is a vacuum tube 36 which is a conventional triode tube having plate, grid and cathode electrodes. Alternatively, a high input impedance transistor, such as a FET, can be used. A grid leak resistor 38 is coupled between the grid and cathode of tube 36 to provide bias current to the grid of tube 36.

The resonant circuit 34 includes a variable capacitor 40 coupled in parallel with a tapped inductor 42. Capacitor 40 can be adjusted to obtain the proper resonant frequency from the resonant circuit 34. For example, the value of inductor 42 and the setting for capacitor 40 can be selected so that the frequency of resonant circuit 34 is between ten and fifty megahertz.

One junction of the parallel combination of capacitor 40 and inductor 42 is coupled directly to the plate of tube 36 and the other junction of capacitor 40 and inductor 42 is coupled through a grid coupling capacitor 44 to the grid of tube 36. In such an oscillator, tube 36 operates in the class C mode. The tap 46 of inductor 42, in effect, results in inductor 42 being two lumped inductances. Thus, the manner in which resonant circuit 34 is coupled with respect to vacuum tube 36 makes the oscillator portion of oscillator/demodulator 24 a conventional Hartley oscillator. The tap 46 of inductor 42 is coupled through a capacitor 48 to ground. Capacitor 48 should be selected to be sufficiently large to act as a short circuit for a.c. voltages of the frequency at which resonant circuit 34 is tuned. In addition, a source of plate voltage Vbb is coupled to one end of a plate resistor 49, the other end of which is coupled to tap 46.

The Coulter transducer 12 schematically can be shown as an aperture resistance 50 coupled in parallel with an aperture capacitance 52. The resistance 50 and capacitance 52 are made up of both the normal resistance and capacitance of orifice 16 plus any additional resistance and/or capacitance added as a result of the presence of a blood cell 20 therein.

Coupling circuit 26 includes an inductor 54 and a capacitor 56. One end of each of inductor 54 and capacitor 56 are coupled together and to the junction between aperture resistance 50 and aperture capacitance 52. The other end of aperture resistance 50 and aperture capacitance 52 are also coupled together and to ground. The other end of inductor 54 is coupled to the end of resistor 30 remote from voltage source 28. The other end of capacitor 56 is coupled to the plate of vacuum tube 36 and to the junction between capacitor 40 and inductor 42. The value of inductor 54 is selected so that inductor 54 acts as a short circuit for the low frequency or d.c. signal provided from source 22 and as a open circuit for oscillator/demodulator 24 signals at the resonant frequency determined by resonant circuit 34. The value of capacitor 56, on the other hand, is selected so that capacitor 56 acts as a short circuit for signals having the resonant frequency determined by resonant circuit 34 and as an open circuit for the d.c. voltage from source 22, the d.c. pulse across transducer 12 and the envelope 57 (discussed hereafter with respect to FIG. 3) of the resonant circuit 34 signal.

As previously mentioned, voltage Vbb is applied through plate resistor 49, tap 46 and the upper half of inductor 42 to the plate of vacuum tube 36. Because inductor 54 is a short circuit to the d.c. voltage and an open circuit to the a.c. voltage and because capacitor 48 is a short circuit for the a.c. voltage and an open circuit to the d.c. voltage, the tap 46 appears as a.c. ground for the oscillator portion of oscillator/demodular 24.

Because both capacitor 56 and capacitor 48 are selected to have values so that they act as short circuits to the high frequency signals from oscillator/demodulator 24, the resistance 50 and capacitance 52 of transducer 12 are in effect coupled in parallel with resonant circuit 34. Thus, the aperture resistance 50 and capacitance 52 are electrically a part of the resonant circuit. This causes the resonant frequency provided by circuit 34 to depend not only upon the values of capacitor 40 and inductor 42, but also upon the values of resistance 50 and capacitance 52. Because of the fact that the resistance 50 and capacitance 52 of transducer 12 are coupled as part of the resonant circuit 34, any changes in resistance 50 or capacitance 52 values due to, for example, a bubble passing through orifice 16 or a change in pressure or temperature of the fluid flowing through orifice 16, will not detune the circuit as was previously the case in the prior art. Rather, a slight effect on the frequency may result, but this change will have negligible effect when utilizing the circuit shown in FIG. 2 to measure opacity.

While a change in the value of capacitance 52 can have little effect on the circuit shown in FIG. 2, a change in the value of resistance 50, due to a blood cell 20 entering orifice 16, will affect the amplitude of the signal provided at tap 46. In effect, by increasing the value of resistance 50, the Q of oscillator portion of oscillator/demodulator 24 is increased. This, in turn, increases the value of the amplitude of the signal appearing at tap 46. This is particularly true where vacuum tube 36 operates as a class C amplifier. The same increase in signal amplitude appears at the plate of tube 36.

Figure 3:
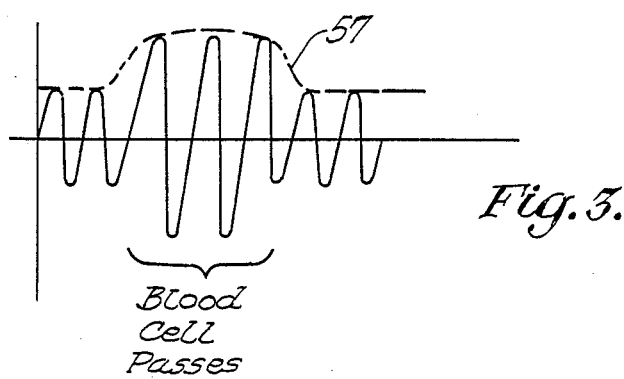
FIG. 3 is a waveform useful in understanding the operation of the circuit shown in FIG. 2.

Referring to FIG. 3, the waveform of the signal at the output of tap 46 is shown as increasing in magnitude whenever a blood cell 20 is present in orifice 16. This is due to the increase in resistance presented by cell 20 and the corresponding increase in the Q of oscillator/demodulator 24. This signal defines the envelope 57, which can be coupled from the tap 46 by a capacitor 58 and amplified by an operational amplifier 60. Simply stated, the signal at the plate of vacuum tube 36 is amplitude modulated by the increased resistance due to a blood cell 20 passing through orifice 16. The maximum amplitude of the envelope 57 signal can be used to determine the a.c. impedance of the cell 20.

Alternatively, the amplitude modulated signal 57 can be obtained by providing the signal applied to the plate of vacuum tube 36 through a coupling capacitor 62, a conventional a.c. demodulator 64, and an output capacitor 66. In taking the envelope signal 57 from tap 46, it is necessary to maintain capacitor 44 at a relatively large value, for example 0.5 microfarads, in order to maintain a fixed grid bias on triode 36 during the particle transient time. Where one utilizes demodulator 64, a smaller capacitor, for example 20 picofarads, can be used to allow the bias on triode 36 to change during the particle transient time.

The presence and magnitude of the pulse created as the d.c. response to a cell traversing through transducer 12 can be detected by applying the output from current source 22 through a coupling capacitor 68 and an operational amplifier 70, in a known manner. The d.c. pulse magnitude is proportional to the d.c. resistance of the cell 20. By applying both the detected d.c. pulse and a.c. pulse to appropriate output means (not shown), the opacity then can be determined in a known manner, such as shown in U.S. Pat. No. 3,509,973 in the name of Wallace H. Coulter, et al.

Thus, it is seen that by coupling the resistance 50 and capacitance 52 of the transducer 12 in parallel with the resonant circuit 34, the effects of short term drifts in the transducer resistance and capacitance have no adverse effects on circuit operation and provide an amplitude modulated output signal due to the changed transducer resistance, and hence changed Q of the circuit. The amplitude modulated signal can be detected directly to provide a reading relating to the reactance of a blood cell 20 passing through the orifice 16.

Figure 4:
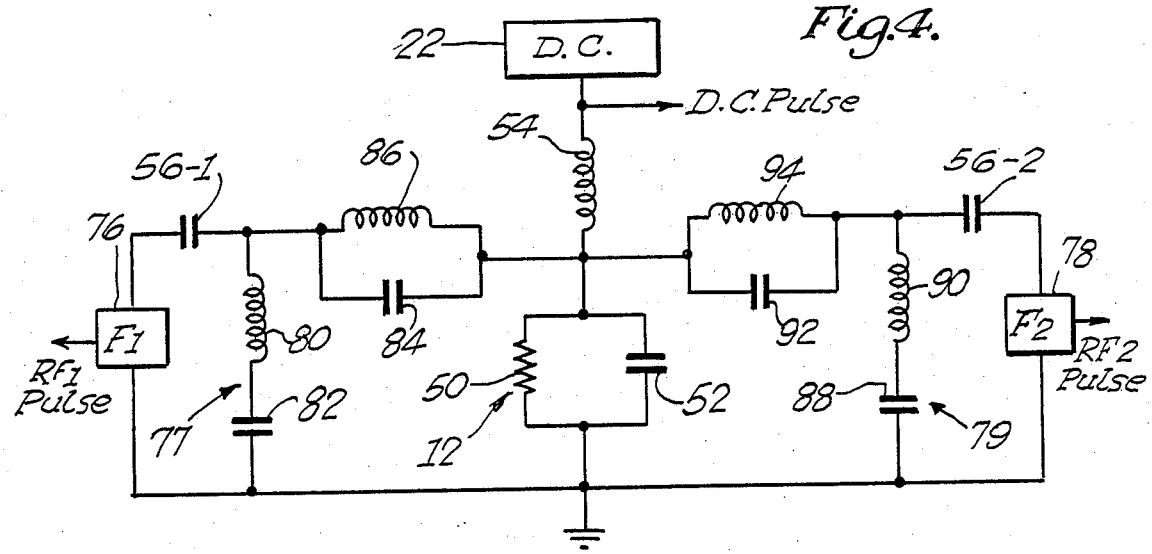
FIG. 4 shows a coupling circuit for coupling two high frequency oscillators in parallel with the particle detector.

Referring now to FIG. 4, a coupling circuit 74 is shown which is useful to couple a pair of RF oscillator/detectors 76 and 78 in parallel with the transducer 12, manifested by resistor 50 and capacitor 52. Oscillators 76 and 78 are coupled in a separate leg 77 and 79 of the circuit shown in FIG. 4, with each leg 77 and 79 being coupled in parallel with transducer 12. In FIG. 4, like numerical designations have been given for like components previously explained in FIGS. 1 and 2. Further, the oscillators 76 and 78 can be similar to oscillator 24 shown in FIGS. 1 and 2, except that they provide different frequencies F1 and F2. Further, the capacitor 56, shown in FIG. 2, is shown as the capacitors 56-1 and 56-2 for each leg. The remaining components, which will be described in detail hereafter, constitute the coupling circuit 74 which is used to couple oscillators 76 and 78 in circuit with the transducer 12.

The reactance and resistance of transducer 12 becomes a part of each respective oscillator 76 and 78, so that the signal magnitudes of the RF1 PULSE and RF2 PULSE signals provided by each oscillator, respectively, will change depending on the response, at the particular frequencies F1 and F2, to cells traveling through orifice 16. The signal magnitude changes then are detected and additional parameters of the blood cell can be determined. In order to obtain reliable data, it is important that the signals of the two oscillators 76 and 78 do not interfere with one another. Thus, the coupling circuit 74 coupling the oscillators 76 and 78 in parallel with transducer 12 must provide two functions. First it must isolate the other oscillators' frequencies, and second, it must couple the oscillator circuitry with transducer 12. In order to accomplish this result, oscillator 76, which is tuned at a frequency F1, has a trap circuit, consisting of an inductor 80 coupled in series with a capacitor 82, coupled in parallel with the series combination of oscillator 76 and capacitor 56-1. This combination of elements is coupled through a tank circuit, consisting of a capacitor 84 coupled in parallel with an inductor 86, to transducer 12. Oscillator 78, which is tuned at a frequency F2, is coupled in series with capacitor 56-2 and these two elements are coupled in parallel with a trap circuit, consisting of a serial coupled capacitor 88 and an inductor 90. This combination of elements is coupled through a tank circuit, consisting of a capacitor 92 and an inductor 94 in parallel, to transducer 12.

In order to prevent interference and the creation of beat frequency signals by the one of the oscillators 76 and 78 external to the leg 77, 79 containing the other one of oscillator 76 and 78, the components of the tank and trap circuit are selected to block the oscillator frequency out of the leg 77, 79 in which they are included. Thus in leg 77, the values of inductor 80 and capacitor 82 are selected to attenuate all signals having the F2 frequency. Similarly, the values of capacitor 84 and inductor 86 are selected to block, or present a high impedance to, signals having the F2 frequency. In the other leg 79, the values of capacitor 88 and inductor 90 are selected to attenuate the F1 frequency and the values of capacitor 92 and inductor 94 are selected to block, or present a high impedance to, the F1 frequencies.

In addition to selecting the inductor and capacitor values discussed above to be of such value to attenuate or block specific frequencies, the values of capacitor 56-1 and 56-2 are selected so that a tight coupling exists between the resistance 50 and capacitance 52 of transducer 12 and the circuitry within each of the respective oscillators 76 and 78. In other words, for signals with frequency F1, the value of capacitor 56-1 should be such that a low impedance path exists between oscillator 76 and transducer 12. Similarly, the value of capacitor 56-2 should be selected so that a low impedance path exists between transducer 12 and oscillator 78 for signals with a frequency of F2.

Thus, with the coupling circuit 74, each of the oscillators 76 and 78 are coupled across transducer 12 independent of and isolated from the other one of oscillators 76 or 78. Further, oscillators 76 and 78 respectively provides an output signal, RF1 PULSE and RF2 PULSE, similar to the signal provided by amplifier 60 of oscillator 24 in FIG. 2, which signal is shown in FIG. 3. Of course, with the coupling circuit 74, any type of oscillator could be used which provides a signal manifesting the response of a blood cell, or other type particle, traveling through transducer 12.

Figure 5:
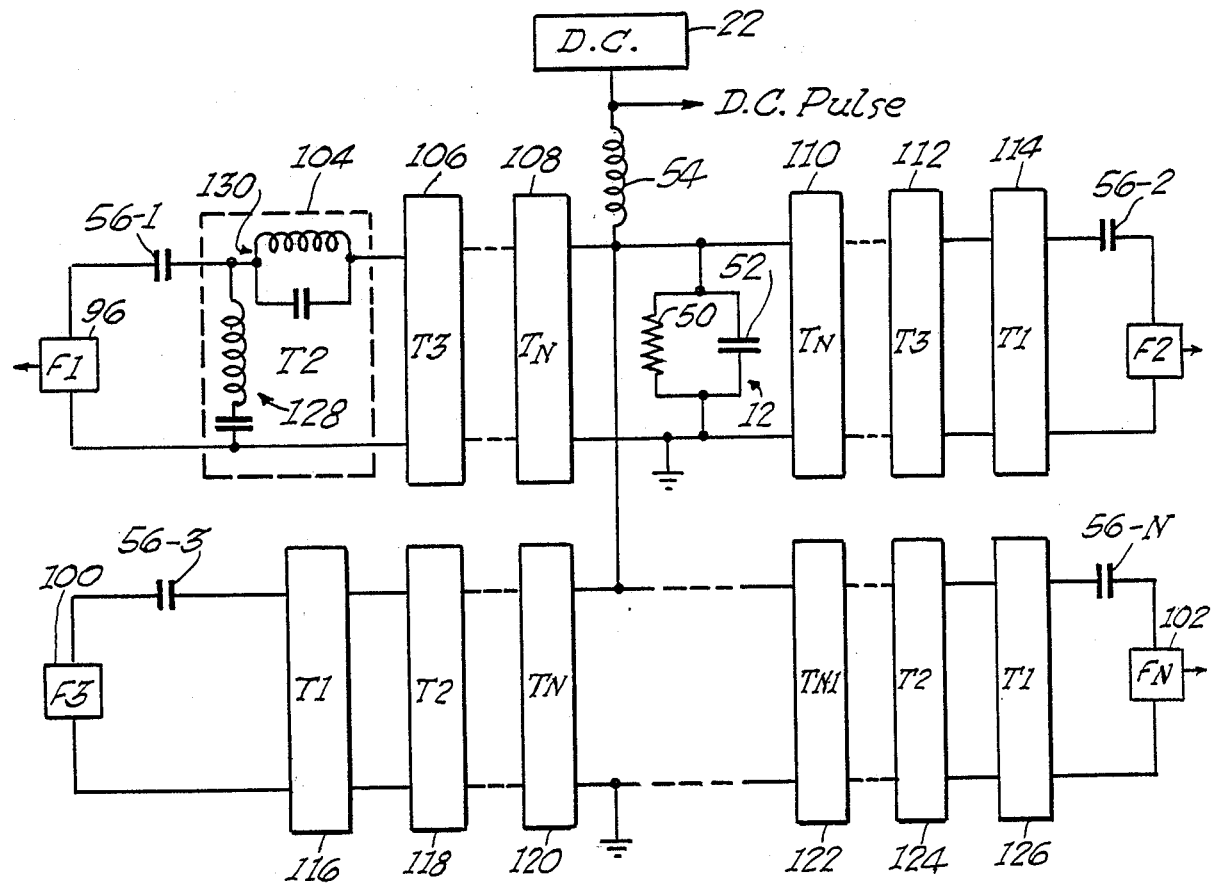
FIG. 5 shows a coupling circuit for coupling any number of oscillators in parallel with the particle detector.

Referring now to FIG. 5, a more generic version of the coupling circuit 74, shown in FIG. 4, is illustrated. In FIG. 5, N different oscillators 96, 98, 100 . . . 102 are provided, each in parallel, through an appropriate coupling circuit, with transducer 12. In each coupling circuit, N-1 coupler circuits 104, 106 . . . 108, 110, 112 . . . 114, 116, 118 . . . 120, and 122, 124 . . . 126, each consisting of a series trap 128 and parallel tank 130 circuit tuned to frequencies of the oscillators external to that leg, are provided. Thus, in the leg associated with oscillator 96, which provides a signal at a frequency F1, the various coupling filters 104, 106 and 108 are respectively tuned to the frequencies F2, F3 . . . FN, as manifested by the notations T2, T3 . . . TN, to prevent signals from the other oscillators 98, 100 . . . 102 from interfering with oscillator 96. The other legs are similar in that a coupling circuit 110, 112 . . . 114, 116, 118, 120 and 122, 124 . . . 126 are each tuned to the frequencies of the oscillators 96, 98, 100 . . . 102 external to that leg. Again, in each case the value of the capacitor 56-1, 56-2, 56-3 . . . 56-N is selected so that a low impedance path is presented for signals having the frequency of the oscillator included in the leg.

Thus, with the coupling as shown in FIG. 5, each of the oscillators 96, 98, 100 and 102 provides a signal manifesting the response of a cell passing through transducer 12 to the particular frequency of that arm. This signal is provided directly from the oscillator, as explained above, with respect to FIG. 3. However, in FIG. 5, multiple different frequency responses can be obtained and, in so doing, different parameters and responses of the particular cell can be determined, whereby better information about the particular cell can be obtained.

What is claimed is:

1. A particular analyzer comprising:
    detector means through which a series of particles pass, said detector means having a certain resistance and reactance, at least one of which changes as a particle passes therethrough;
    oscillator means, including an active device and a resonant circuit, said resonant circuit being coupled to said detector means so that said detector means resistance and reactance are included as a part of said resonant circuit; and
    means for sensing any change in the output signal of said oscillator as a result of a particle passing through said detector means.

2. The invention according to claim 1 wherein said analyzer further includes steady-state current providing means for providing a steady state current through said detector means.

3. The invention according to claim 2 wherein said analyzer further includes isolation means for isolating said steady-state current providing means and said oscillator means.

4. The invention according to claim 1 wherein said oscillator means is coupled to said detector means to provide a high frequency current through said detector means.

5. The invention according to claim 4 wherein said analyzer further includes second current providing means coupled to provide a second current through said detector means.

6. The invention according to claim 5 wherein said oscillator means and said second current providing means are coupled to said detector means through isolation means.

7. The invention according to claim 6:
    wherein said second current providing means is a d.c. current source;
    wherein said oscillator means is a high frequency oscillator; and
    wherein said isolation means includes an inductor coupled in series between said d.c. current source and said detector means and a capacitor coupled in series between said resonant circuit and said detector means.

8. The invention according to claim 1 wherein said means for sensing is coupled to said resonant circuit.

9. The invention according to claim 1 wherein said means for sensing is coupled between said active device and said resonant circuit.

10. The invention according to claim 1 wherein said detector means resistance and reactance are coupled in parallel with said resonant circuit.

11. The invention according to claim 1:
    wherein said oscillator means includes at least two oscillators, each having a resonant circuit, for providing signals at two different frequencies; and
    wherein each of said oscillators are coupled to said detector means so that said detector means resistance and reactance is included as a part of the resonant circuit thereof.

12. The invention according to claim 11 wherein each of said oscillators are coupled to said detector through filter means associated therewith for eliminating any signal having a frequency of the signal provided by the other of said oscillators.

13. The invention according to claim 12 wherein each of said filter means includes a tank circuit coupled in series with said detector and the one of said oscillators with which the filter means is associated.

14. The invention according to claim 13 wherein said tank circuit is tuned to the frequency of the other of said oscillators.

15. The invention according to claim 12 wherein each of said filter means includes a trap circuit coupled in parallel with the one of said oscillators with which that filter means is associated.

16. The invention according to claim 15 wherein said trap circuit is tuned to the frequency of the other of said oscillators.

17. A blood cell analyzer which determines the presence of blood cells and for providing data to allow the determination of the opacity of the detected cells comprising:
cell transporting means, including first and second chambers separated by a small orifice, said blood cells flowing from said first chamber to said second chamber through said orifice;
a direct current (d.c.) current source;
means for coupling said current source to said orifice to provide d.c. current through said orifice and a d.c. voltage across said orifice;
an oscillator, including an active device and a resonant circuit;
means for coupling said resonant circuit in parallel with said orifice, to provide an alternating current (a.c.) signal through said orifice;
means for sensing the change in the d.c. voltage across said orifice; and
means for sensing the amplitude of the a.c. signal provided by said resonant circuit.

18. The invention according to claim 17 wherein said means for coupling said current source includes inductance means sized to act as a short circuit for said d.c. current and an open circuit to said a.c. signal.

19. The invention according to claim 18 wherein said means for coupling said resonant circuit includes capacitance means sized to act as a short circuit for said a.c. signal and an open circuit to said d.c. current.

20. The invention according to claim 17 wherein said oscillator resonant circuit includes a pair of series coupled reactances of one type coupled in parallel with a reactance of opposite type, an envelope of said a.c. signal provided by said resonant circuit being provided from between said series coupled reactances of one type.

21. The invention according to claim 17:
wherein said analyzer further includes a second oscillator having an active device and a resonant circuit and means for coupling said resonant circuit of said second oscillator in parallel with said orifice;
wherein said means for coupling said resonant circuit of said first mentioned oscillator includes first filter means to isolate said first oscillator from any signals having frequencies of said second oscillator; and
wherein said means for coupling said resonant circuit of said second oscillator includes second filter means to isolate said second oscillator from signals having frequencies of said first oscillator.

22. The invention according to claim 21 wherein each of said resonant circuits further includes associated capacitance means sized to couple, through a low impedance path including said filter means, said orifice to the resonant circuit with which that capacitance means is associated.

23. The invention according to claim 21 wherein said first and second filter means each include a tank circuit and a trap circuit, said tank circuit being coupled in series between an oscillator and said orifice and said trap circuit being coupled in parallel across an oscillator.

24. A blood cell analyzer for determining the presence of blood cells in a sample under test comprising:
cell transporting means, including first and second chambers separated by a small orifice, said blood cells flowing from said first chamber to said second chamber through said orifice;
an oscillator, including an active device and a resonant circuit, which provides an alternate current;
means for coupling said resonant circuit in parallel with said orifice to provide said alternating current signal through said orifice; and
means for sensing the envelope amplitude of said alternating current signal provided by said resonant circuit.

25. The invention according to claim 24:
wherein said resonant circuit includes a pair of series coupled reactances of one type coupled in parallel with a reactance of opposite type; and
wherein said envelope amplitude of said alternating current signal is provided from between said series coupled reactances of one type.

26. A particle analyzer for determining the presence and certain parameters of particles in a solution, comprising:
detector means through which said solution passes, said detector means having a certain resistance and reactance, at least one of which changes as a particle passes therethrough;
a plurality of oscillator means, each providing a different frequency signal;
coupling means for coupling each of said oscillator means in parallel with said detector means, said coupling means including reactance means, associated with each oscillator means, arranged and valued so that the signal provided by each oscillator means is coupled through a low impedance path to said detector means and through a high impedance path to the other of said plurality of oscillator means; and
means for manifesting the presence of said certain parameters for each of said frequencies, whenever a particle passes through said detector means.

27. The invention according to claim 26 wherein said coupling means reactance means includes a tank circuit coupled in series between each oscillator means and said detector means.

28. The invention according to claim 27 wherein each tank circuit is tuned to the frequency of the oscillator means to which it is not coupled.

29. The invention according to claim 26 wherein said coupling means includes a trap circuit coupled in parallel with each oscillator means.

30. The invention according to claim 29 wherein said trap circuit is tuned to the frequency of the oscillator means with which it is not coupled.

31. The invention according to claim 26 wherein said coupling means reactance means includes capacitance means associated with and coupled in series between each oscillator means and said detector means.

32. The invention according to claim 31 wherein said reactance means further includes a tank circuit coupled in series between each capacitance means and said detector means, the values of each capacitance means and said tank circuit being selected so that a low impedance path exists for signals of a frequency the same as the signals provided by said associated oscillator means.

33. The invention according to claim 32 wherein said reactance means further includes a trap circuit coupled in parallel with each oscillator and associated capacitance means, the values of the components of said tank circuit and trap circuit being selected to present a high impedance for signals having frequencies other than the frequency of the signal provided by the associated oscillator and to present a low impedance for signals having a frequency the same as the signal provided by said associated oscillator.

* * * * *

UNITED STATES PATENT AND TRADEMARK OFFICE
CERTIFICATE OF CORRECTION

PATENT NO. : 4,791,355
DATED : December 13, 1988
INVENTOR(S) : Wallace H. Coulter et al.

It is certified that error appears in the above—identified patent and that said Letters Patent is hereby corrected as shown below:

Title page:

Other Publications, 2nd Reference, change "1983" to --1985--;
Other Publications, 8th Reference, change "O'Tonski" to --O'Konski--;
change "Schaffer" to --Scheffer--;
change "Superregenative" to --Superregenerative--;
Other Publications, 9th Reference, change "Yogi" to --Yagi--;
Column 4, line 11, change "demodulatro" to --demodulator--;
Column 5, line 12, change "demodular" to --demodulator--;
Column 8, line 10, change "particular" to --particle--.

Signed and Sealed this

Twenty-ninth Day of October, 1991

Attest:

HARRY F. MANBECK, JR.

Attesting Officer

Commissioner of Patents and Trademarks